United States Patent [19]

Lang et al.

[11] Patent Number: 4,731,200

[45] Date of Patent: Mar. 15, 1988

[54] ALCOHOLIC OR AQUEOUS-ALCOHOLIC COMPOSITIONS CONTAINING NATURAL ESSENCES AND BENZYLIDENE-CAMPHOR DERIVATIVES

[75] Inventors: Gerard Lang, Saint Gratien; Andre Deflandre, Orry-la-Ville; Irena Beck, Villepinte, all of France

[73] Assignee: L'Oreal, Paris, France

[21] Appl. No.: 885,392

[22] Filed: Jul. 18, 1986

Related U.S. Application Data

[63] Continuation of Ser. No. 573,145, Jan. 23, 1984, abandoned.

[30] Foreign Application Priority Data

Jan. 26, 1983 [LU] Luxembourg ............................ 84607

[51] Int. Cl.⁴ ............................ A61K 7/46; C11B 9/00
[52] U.S. Cl. ........................................ 512/5; 424/59
[58] Field of Search ........................... 252/522; 424/59

[56] References Cited

U.S. PATENT DOCUMENTS

| | | | |
|---|---|---|---|
| 3,781,417 | 12/1973 | Welters et al. | 424/59 |
| 4,061,730 | 12/1977 | Kalopisis et al. | 424/59 |
| 4,165,336 | 8/1979 | Bouillon et al. | 260/511 |
| 4,250,108 | 2/1981 | Bouillon et al. | 260/511 |
| 4,290,974 | 9/1981 | Bouillon et al. | 260/511 |
| 4,304,730 | 12/1981 | Bouillon et al. | 260/429.9 |
| 4,323,549 | 4/1982 | Bouillon et al. | 424/45 |
| 4,327,031 | 4/1982 | Bouillon et al. | 260/429.9 |
| 4,330,488 | 5/1982 | Bouillon et al. | 260/511 |
| 4,406,880 | 9/1983 | Bouillon et al. | 424/40 |
| 4,421,739 | 12/1983 | Bouillon et al. | 424/47 |

FOREIGN PATENT DOCUMENTS

| | | | |
|---|---|---|---|
| 1492322 | 1/1970 | Fed. Rep. of Germany . | |
| 1024465 | 4/1953 | France . | |
| 7137119 | 9/1972 | France . | |
| 7334140 | 4/1974 | France . | |
| 2204396 | 5/1974 | France | 424/59 |
| 7424111 | 2/1975 | France . | |
| 7405427 | 7/1975 | France . | |
| 7428478 | 3/1976 | France . | |
| 7527602 | 11/1976 | France . | |
| 7623799 | 3/1978 | France . | |
| 7707720 | 10/1978 | France . | |
| 7727343 | 4/1979 | France . | |
| 7735828 | 6/1979 | France . | |
| 7810158 | 11/1979 | France . | |
| 7820701 | 2/1980 | France . | |
| 0110535 | 7/1983 | Japan | 424/59 |
| 1573370 | 8/1980 | United Kingdom . | |

OTHER PUBLICATIONS

Chemical Abstracts 86:66414v, Phototoxicity of Methoxsalen in Various Vehicles, Suhonen, R., Contact Dermatitis, 1976, 2(5), 264–8, (Eng.).

Chemical Abstracts 95:156354r, Study of the Photochemical Behavior of Sunscreens—Benzylidene Camphor and Derivatives, Beck et al., Int. J. Cosmet. Sci., 1981, 3(3), 139–52, (Eng.).

Primary Examiner—Helen M. S. Sneed
Attorney, Agent, or Firm—Fleit, Jacobson, Cohn & Price

[57] ABSTRACT

The present invention relates to an alcoholic or aqueous-alcoholic composition comprising a natural essence containing a phototoxic dose of furocoumarin, and 0.01 to 2% by weight of at least one benzylidenecamphor derivative filtering out UV-A radiation and chosen from among 3-p-oxybenzylidenebornan-2-ones, 3,3'-terephthalylidenedicamphors optionally sulphonated in the 10-position of the camphor, p-(3-methylidenecamphor)cinnamic acid derivatives, 3,3'-terephthalylidenedicampho-10-sulphonamides or 3,3'-terephthalylidenedicampho-10,10'-disulphonamides. It is also possible to incorporate into the composition a UV-B filter chosen from among benzylidenecamphor, p-methylbenzylidenecamphor, benzylidenecamphor derivatives containing a quaternary ammonium radical on the benzene nucleus in the para position relative to the bornylidene radical, benzylidenecamphor derivatives sulphonated on the methyl radical in the 10-position of the camphor or in the 3'-position or 4'-position on the benzene nucleus, p-methylbenzylidenecamphor derivatives substituted on the p-methyl group, or other 3-benzylidenecamphor derivatives filtering out UV-B radiation.

Application: perfumes, toilet waters, eaux de cologne and shaving lotions.

18 Claims, No Drawings

ALCOHOLIC OR AQUEOUS-ALCOHOLIC COMPOSITIONS CONTAINING NATURAL ESSENCES AND BENZYLIDENE-CAMPHOR DERIVATIVES

This application is a continuation of application Ser. No. 573,145, filed Jan. 23, 1984, now abandoned.

The present invention relates to alcoholic or aqueous-alcoholic compositions, in particular of the toilet water, perfume or shaving lotion type, containing natural essences and benzylidenecamphor derivatives.

It has been known for a very long time that natural essences such as bergamot oil and lemon oil, contained in various cosmetics, perfumes and toilet water, are involved in certain skin diseases which appear as violent erythemas and eczematoid lesions, followed by non-uniform residual pigmentations. These skin reactions, which require exposure to ultraviolet light, are referred to as "phototoxic reactions". The compounds responsible for this phototoxicity are furocoumarins, the main representative of this family in bergamot oil being bergaptene, or 5-methoxyfurocoumarin, or alternatively 5-methoxypsoralene (5-MOP), of the formula:

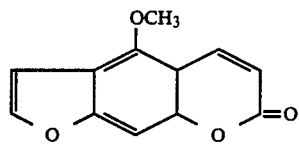

This compound is phototoxic, as are the majority of linear furocoumarins such as, for example, furocoumarin itself and 8-methoxyfurocoumarin. 5-Methoxyfurocoumarin is responsible for skin reactions at a concentration of 10 ppm or above, which explains that, to prevent any risk of skin disease, the use of more than 0.1 to 0.3% of bergamot oil on the skin is generally avoided, this oil containing 3000 to 7500 ppm of 5-methoxyfurocoumarin.

This shows the advantage of removing the furocoumarins from natural essences such as bergamot oil and lemon oil, in order to protect the health of people induced to using toilet waters or perfumes containing such essences.

On account of the economic importance of natural essences, detoxification methods have been proposed, in particular for bergamot oil. These methods employ vacuum distillation of the volatile fraction of the bergamot oils; the distillation residue is then saponified with alcoholic potassium hydroxide in order to convert the furocoumarins to cinnamic acid derivatives by opening of the lactone group, and then extracted with a hydrocarbon after the alcohol has been evaporated off; the extraction solution is neutralised by washing with water, and the residue obtained after the solvent has been evaporated off is incorporated into the volatile fraction.

The bergamot oils treated by this process and containing 40 ppm or less of 5-methoxyfurocoumarin are only very slightly phototoxic, as shown in the publication by J. Girard et al. in "Parfums, cosmetiques, aromes" no. 38, April–May 1981, pages 39–44. However, such methods for the detoxification of natural essences are complicated and expensive and have the disadvantage of considerably modifying the olfactory properties of the essences treated.

Attempts have therefore been made to find another means of detoxifying natural essences by eliminating the toxic effect due to furocoumarins.

It is known that, when furocoumarins absorb ultraviolet light, they are electronically excited. It is the triplet excited level which is the precursor state of all known photobiological reactions.

Now, the Applicants have observed that, totally surprisingly, certain benzylidenecamphor derivatives which filter out UV-A radiation are capable of deactivating the triplet level of furocoumarins according the equation:

Pso denoting psoralene and Bz-C denoting the benzylidenecamphor derivative.

This results in a molecule of furocoumarin in the unexcited ground state and an excited molecule of benzylidenecamphor derivative, which then deactivates itself without any reaction other than a purely intramolecular E-Z isomerization:

The experiments carried out by the Applicants have shown that a concentration of benzylidenecamphor derivative of the order of $4.10^{-3}$ mol per liter is sufficient to deactivate 80% of the excited furocoumarin molecules. Under these conditions, the phototoxic activity of a solution containing a furocoumarins and $4.10^{-3}$ mol per liter of benzylidenecamphor derivative would be 5 times lower than the phototoxic activity of an identical solution not containing benzylidenecamphor derivative.

The object of the present invention is therefore to reduce the phototoxicity of the furocoumarins contained in natural essences by the addition of benzylidenecamphor derivatives filtering out UV-A radiation, which have the property of picking up the electronic excitation energy of the furocoumarins and degrading it in the form of heat energy after isomerisation.

The present invention relates to alcoholic or aqueous-alcoholic compositions containing a phototoxic dose of furocoumarin and at least one benzylidenecamphor derivative filtering out UV-A radiation and chosen from amongst:

the 3-p-oxybenzylidenebornan-2-ones of French Pat. No. 2,430,938, having the formula:

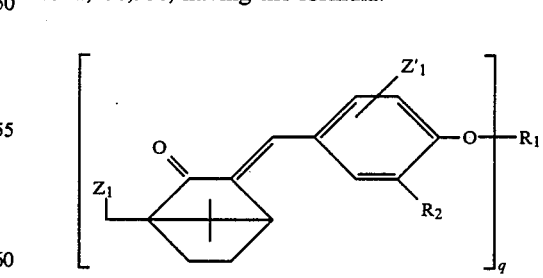

in which:

$Z_1$ and $Z'_1$ respectively denote a hydrogen atom, a radical $SO_3H$ or a salt of this sulphonic acid with an inorganic or organic base, at least one of the two radicals $Z_1$ or $Z'_1$ representing a hydrogen atom;

$R_1$ denotes a hydrogen atom, an optionally branched alkyl radical containing 2 to 18 carbon atoms, an alkenyl radical containing 3 to 18 carbon atoms or a radical

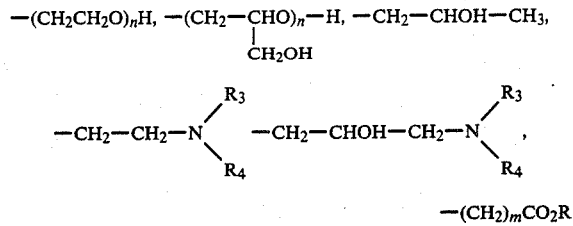

$-(CH_2)_m CO_2 R$ in which R denotes H, an alkyl radical containing 1 to 8 carbon atoms, $-(CH_2)_3-SO_3H$ or a salt of this acid with an organic or inorganic base, or alternatively a divalent radical $-(CH_2)_m-$ or $-CH_2-CHOH-CH_2-$, m having the values 1 to 10 and n having the values 1 to 6, and $R_3$ and $R_4$ each representing a hydrogen atom or an optionally branched or hydroxylated alkyl radical, or together forming an aminoaliphatic heterocycle with the nitrogen atom;

$R_2$ denotes a hydrogen atom, an alkoxy radical containing 1 to 4 carbon atoms or a divalent radical $-O-$ joined to the radical $R_1$ in the case where the latter is also divalent; and q denotes 1 or 2, it being understood that if q has the value 2, $R_1$ is a divalent radical, and that if $R_1$ denotes hydrogen, $R_2$ also denotes hydrogen; moreover, if $R_2$ denotes alkoxy, $R_1$ can also denote methyl;

the benzylidenecamphors described in Belgian Patent Application No. 211,002, having the formula:

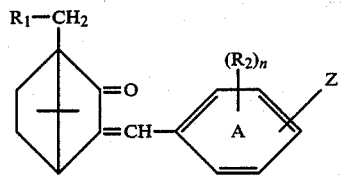

in which:
$R_1$ denotes a hydrogen atom or a radical $-SO_3^\ominus M^\oplus$, in which M denotes a hydrogen atom, an alkali metal or a group $N^\oplus(R_3)_4$, $R_3$ denoting a hydrogen atom or a $C_1$ to $C_4$ alkyl or hydroxyalkyl radical;
n=0, that is to say $R_2$ denotes a hydrogen atom; and
Z represents a group

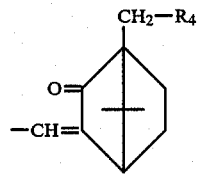

in which $R_4$ has the same meanings as $R_1$ and can be equal to $R_1$ or different from $R_1$, or alternatively a group

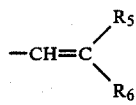

in which $R_5$ denotes a hydrogen atom, a $C_1$ to $C_4$ alkyl radical, an aryl radical optionally substituted by halogen atoms or by $C_1$ to $C_4$ alkyl or alkoxy groups, or a group $-CN$, $-COOR_7$ or

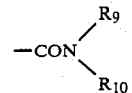

and $R_6$ denotes a group $-COOR_8$ or

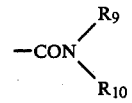

$R_7$ and $R_8$, which are identical or different, being alkyl, alkenyl, cycloalkyl or aralkyl radicals containing at most 20 carbon atoms, which are optionally substituted by hydroxyl, alkoxy, amine or quaternary ammonium groups, and $R_9$ and $R_{10}$, which are identical or different, denoting a hydrogen atom or alkyl, alkenyl, cycloalkyl or aralkyl radicals containing at most 20 carbon atoms, which are optionally substituted by hydroxyl, alkoxy, amine or quaternary ammonium groups, or alternatively if $R_5$ denotes a hydrogen atom or an alkyl or optionally substituted aryl radical, $R_6$ can also represent a radical $-COO^\ominus M^\oplus$, M being defined as above, the two methylidenecamphor radicals, on the one hand, and Z, on the other hand, being attached to the aromatic nucleus A in the para position relative to one another; and the sulphonamides derived from benzylidenecamphor described in Belgian Patent Application No. 211,134, having the formula:

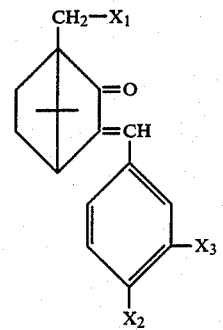

in which:
$X_1$ denotes the radical Y;
$X_2$ denotes a radical Z; and
$X_3$ denotes a hydrogen atom,
Y denoting the group

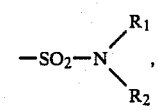

in which $R_1$ denotes a hydrogen atom or a $C_1$-$C_4$ alkyl or hydroxyalkyl radical and $R_2$ denotes a hydrogen atom, a linear or branched alkyl or alkenyl radical or a cycloalkyl, aryl or aralkyl radical, it being possible for these various $C_1$-$C_{20}$ radicals to be substituted by one or more hydroxyl, alkoxy or dialkylamino groups, it being impossible for $R_1$ and $R_2$ simultaneously to denote a hydrogen atom, and Z denoting one of the following groups:

$Z_1 =$

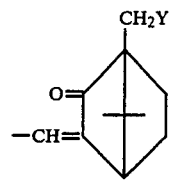

in which Y has the abovementioned meaning, or $Z_2 =$

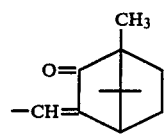

A phototoxic dose can be defined as being equal to at least 10 ppm of bergaptene.

Experiments carried out on guinea-pigs have made it possible to demonstrate the considerable reduction in erythema or the absence of erythema on the skin to which the composition has been applied, after the animal has been exposed to UV-A radiation.

The following may be mentioned as particularly preferred compounds filtering out UV-A radiation which are used according to the invention: 3,3'-terephthalylidenecampho-10,10'-disulphonic acid, 3,3'-terephthalylidenecampho-10-sulphonic acid, 4-(ethyl 2'-carboxyethylacrylate)-benzylidenecamphor, 4'-butoxy-3'-methoxy-3-benzylidenebornanone and also their salts.

According to a preferred embodiment of the invention, the alcoholic or aqueous-alcoholic composition containing a phototoxic dose of furocoumarin and at least one benzylidenecamphor derivative filtering out UV-A radiation also contains at least one compound filtering out UV-B radiation which is compatible with the abovementioned UV-A filters.

The compounds filtering out UV-B radiation are chosen from amongst:

benzylidenecamphor;

p-methylbenzylidenecamphor;

benzylidenecamphor derivatives containing a quaternary ammonium radical on the benzene nucleus in the para position relative to the bornylidene radical, according to French Pat. No. 2,199,971, having the formula:

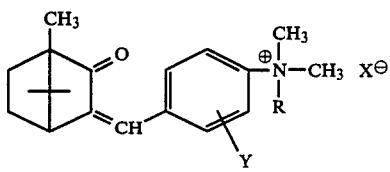

in which:

R represents a hydrogen atom or an alkyl group containing 1 to 12 carbon atoms,

Y represents a halogen, a methyl group or a hydrogen atom, and $X^{\ominus}$ represents a halide, an arylsulphonate, an alkylsulphonate, a camphosulphonate or an alkylsulphate;

benzylidenecamphor derivatives sulphonated on the methyl radical in the 10-position of the camphor or in the 3'-position or 4'-position on the benzene nucleus, according to French Pat. No. 2,236,515 and No. 2,282,426, respectively having the formulae:

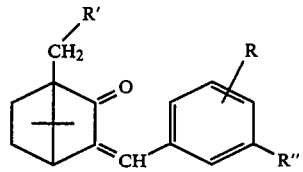

in which R denotes a hydrogen atom, a halogen atom such as Cl or F, or an alkyl radical containing 1 to 4 carbon atoms, and R' and R" each denote a hydrogen atom or a radical —$SO_3M$, in which M denotes H, an organic ammonium group or a metal, at least one of the radicals R' and R" not having the meaning H, and

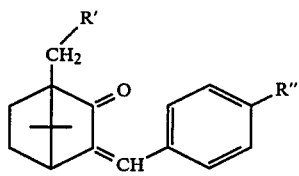

in which R' denotes a hydrogen atom or a radical —$SO_3M$ and R" denotes $SO_3M$, in which M denotes H, an organic ammonium group or a metal;

p-methylbenzylidenecamphor derivatives substituted on the p-methyl group, according to French Pats. No. 2,383,904, No. 2,402,647 and No. 2,421,878, respectively having the formulae:

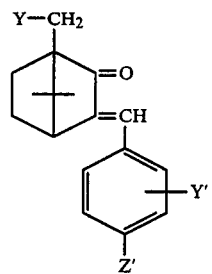

in which Y and Y' denote H or $SO_3H$ and the corresponding salts with organic or inorganic bases, at least one of the radicals Y and Y' having the meaning H; and Z' denotes the group —$CH_2R$, —$CHR'R'$, —CHO or —COOR", in which R=—$OR_4$, —$OCOR_5$, —$SR_6$, —CN or —COOR", $R_4$=H, alkyl, polyoxyethylene or substituted or unsubstituted aryl, $R_5$=alkyl, alkenyl, aryl or an aromatic or non-aromatic heterocycle containing 5 to 6 ring members, and $R_6$=H, alkyl, carboxyalkyl, aminoalkyl, hydroxyalkyl, aryl or alanin-3-yl, $R'=OR'_4$ or —$SR'_6$, in which $R'_4$ and $R'_6$ can respectively have the same meanings as $R_4$ and $R_6$, except for the meaning hydrogen, and R"=hydrogen or alkyl, and

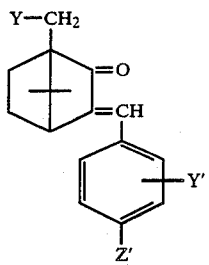

in which Y denotes H or SO₃H and the corresponding salts with organic or inorganic bases;
Y' denotes H; and
Z' denotes the group —CH$_2$I, —CH$_2$R, —CHR'R', —CHO or —COOR", in which R=—OR$_4$, —OCOR$_5$, —SR$_6$, —CN or —COOR", R$_4$=H, alkyl, polyoxyethylene, substituted or unsubstituted aryl, menthyl or dialkylaminoalkyl, R$_5$=alkyl, alkenyl, aryl or an aromatic or non-aromatic heterocycle containing 5 to 6 ring members and R$_6$=H, alkyl, carboxyalkyl, aminoalkyl, hydroxyalkyl, aryl or alanin-3-yl, R'=—OR'$_4$ or —SR'$_6$, in which R'$_4$ and R'$_6$ can respectively have the same meanings as R$_4$ and R$_6$, except for the meanings hydrogen, polyoxyethylene, hydroxyalkyl, alanin-3-yl and aryl, and R"=hydrogen or alkyl;

the benzylidenecamphors described in Belgian Patent Application No. 211,002, having the formula:

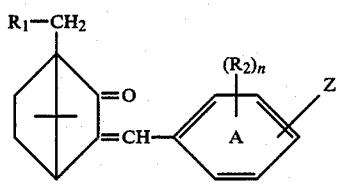

in which:
R$_1$ denotes a hydrogen atom or a radical —SO$_3$⊖M⊕, in which M denotes a hydrogen atom, an alkali metal or group N⊕(R$_3$)$_4$, R$_3$ denoting a hydrogen atom or a C$_1$ to C$_4$ alkyl or hydroxyalkyl radical;
R$_2$ denotes a linear or branched C$_1$ to C$_4$ alkyl radical or a C$_1$ to C$_4$ alkoxy radical, n being an integer ranging from 0 to 4; if n≧2, the radicals R$_2$ can be identical or different; and Z represents a group

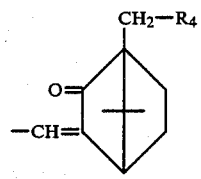

in which R$_4$ has the same meanings as R$_1$ and can be equal to R$_1$ or different from R$_1$, or alternatively a group

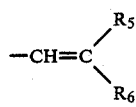

in which R$_5$ denotes a hydrogen atom, a C$_1$ to C$_4$ alkyl radical, an aryl radical optionally substituted by halogen atoms or by C$_1$ to C$_4$ alkyl or alkoxy groups, or a group —CN, —COOR$_7$ or

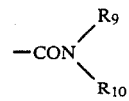

and R$_6$ denotes a group —COOR$_8$ or

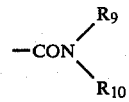

R$_7$ and R$_8$, which are identical or different, being alkyl, alkenyl, cycloalkyl or aralkyl radicals containing at most 20 carbon atoms, which are optionally substituted by hydroxyl, alkoxy, amine or quaternary ammonium groups, and R$_9$ and R$_{10}$, which are identical or different, denoting a hydrogen atom or alkyl, alkenyl, cycloalkyl or aralkyl radicals containing at most 20 carbon atoms, which are optionally substituted by hydroxyl, alkoxy, amine or quaternary ammonium groups, or alternatively if R$_5$ denotes a hydrogen atom or an alkyl or optionally substituted aryl radical, R$_6$ can also represent a radical —COO⊖M⊕, M being defined as above,
the two methylidenecamphor radicals, on the one hand, and Z, on the other hand, being attached to the aromatic nucleus A in the meta position relative to one another; they can be attached in the para position if n≠0; and the sulphonamides derived from benzylidenecamphor described in Belgian Patent Application No. 211,134, having the formula:

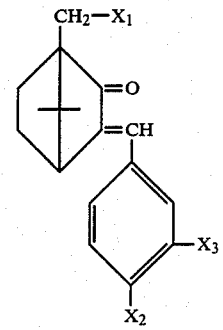

in which X$_1$ denotes a hydrogen atom or the radical Y; X$_2$ denotes a hydrogen or halogen atom, a C$_1$–C$_4$ alkyl or alkoxy radical or a radical Y or Z; and X$_3$ denotes a hydrogen or halogen atom, a C$_1$–C$_4$ alkyl or alkoxy radical or a radical Y or Z, or alternatively X$_2$ and X$_3$ together form an alkylenedioxy group in which the alkylene group contains 1 or 2 carbon atoms, Y denoting the group

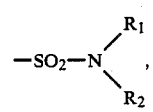

in which R$_1$ denotes a hydrogen atom or a C$_1$–C$_4$ alkyl or hydroxyalkyl radical and R$_2$ denotes a hydrogen atom, a linear or branched alkyl or alkenyl radical or a cycloalkyl, aryl or aralkyl radical, it being possible for these various $C_1$–$C_{20}$ radicals to be substituted by one or more hydroxyl, alkoxy or dialkylamino groups, it being impossible for $R_1$ and $R_2$ simultaneously to denote a hydrogen atom, and Z denoting one of the following groups:

$Z_1 =$

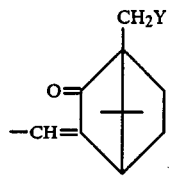

in which Y has the abovementioned meaning, or $Z_2 =$

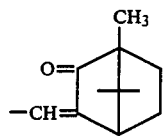

or
$Z_3 =$

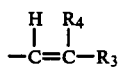

in which $R_3$ denotes a hydrogen atom or a group —CN or —$COR_5$ and $R_4$ denotes a group —$COR_6$, $R_5$ and $R_6$, which are identical or different, being $C_1$–$C_{20}$ alkoxy or alkylamino groups,
with the proviso that one of the symbols $X_1$, $X_2$ and $X_3$ is different from the other two and that (a) when $X_1$ denotes a hydrogen atom, $X_2$ and $X_3$ are different from one another and cannot take the meanings $Z_2$ and $Z_3$, one of the two necessarily having the meaning Y or $Z_1$, and (b) when $X_1$ has the meaning Y, $X_2$ and $X_3$ are different from Y and cannot simultaneously take the meaning $Z_1$, $Z_2$ or $Z_3$, and, moreover, if $X_2 = Z_1$ or $Z_2$, $X_3$ does not denote a hydrogen atom.

The following may be mentioned as particularly preferred compounds filtering out UV-B radiation: benzylidenecamphor, 4-[(2-oxo-3-bornylidene)-methyl]-phenyltrimethylammonium methyl-sulphate, p-methylbenzylidenecamphor, N-(2-ethylhexyl)-3-benzylidenecampho-10-sulphonamide, 3-benzylidene-2-oxobornane-10-sulphonic acid, 3-(2-oxo-3-bornylidenemethyl)-benzenesulphonic acid, 2-methyl-5-(2-oxo-3-bornylidenemethyl)benzenesulphonic acid and also their salts.

The alcoholic or aqueous-alcoholic composition according to the invention can consist of an eau de cologne, a toilet water, a perfume or a pre-shave or after-shave lotion containing natural essences such as bergamot oil and lemon oil.

It generally contains 0.01 to 2% and preferably 0.1 to 1% by weight of benzylidenecamphor derivative(s).

The pre-shave or after-shave lotions, eaux de cologne and toilet waters are presented in the form of an aqueous-alcoholic solution containing, apart from the natural essence and the benzylidenecamphor or one of its derivatives, a lower alkanol containing 1 to 4 carbon atoms, preferably ethanol or isopropanol and, if appropriate, n-propanol, and glycols such as ethylene glycol or propylene glycol, and comprising the adjuvants normally used, such as softeners, for example glycerol, and cicatrising agents, as well as preservatives.

The composition according to the invention can also be an alcoholic or aqueous-alcoholic gel comprising, in addition to natural essences, one or more lower alcohols such as ethanol, propylene glycol or glycerol, and a thickener, if appropriate in the presence of water.

The alcoholic or aqueous-alcoholic composition according to the invention will be illustrated more clearly by the non-limiting examples which follow.

EXAMPLE 1

| Perfume | |
|---|---|
| Natural essence containing 5% of bergamot oil | 25 g |
| Triethanolamine salt of 3,3'-terephthalylidenedicampho-10,10'-disulphonic acid | 0.5 g |
| Distilled water | 0.2 g |
| 96.2° strength alcohol q.s. | 100 cm³ |

The perfume formulated in this way contains 43.7 ppm of 5-MOP.

EXAMPLE 2

| Perfume | |
|---|---|
| Natural essence containing 5% of bergamot oil | 20.5 g |
| Triethanolamine salt of 3,3'-terephthalylidenedicampho-10-sulphonic acid | 0.3 g |
| Benzylidenecamphor | 0.1 g |
| Distilled water | 0.2 g |
| 96.2° strength alcohol q.s. | 100 cm³ |

The perfume formulated in this way contains 35.8 ppm of 5-MOP.

EXAMPLE 3

| Toilet water | |
|---|---|
| Natural essence containing 30% of bergamot oil | 8 g |
| Triethanolamine salt of 3,3'-terephthalylidenedicampho-10,10'-disulphonic acid | 0.55 g |
| N—(2-ethylhexyl)-3-benzylidene-10-camphosulphonamide | 0.4 g |
| Distilled water | 4.3 g |
| 96.2° strength alcohol q.s. | 100 cm³ |

The toilet water formulated in this way contains 84 ppm of 5-MOP.

EXAMPLE 4

| Eau de cologne | |
|---|---|
| Natural essence containing 50% of bergamot oil | 1.5 g |
| 4'-butoxy-3'-methoxy-3-benzylidene-bornanone | 0.2 g |
| 4-[(2-oxo-3-bornylidene)-methyl]-phenyltrimethylammonium methyl-sulphate | 0.2 g |
| Distilled water | 28.3 g |

| Eau de cologne | |
|---|---|
| 96.2° strength alcohol q.s. | 100 cm³ |

This eau de cologne contains 26.25 ppm of 5-MOP.

We claim:

1. Detoxified alcoholic or aqueous-alcoholic composition in a form selected from the group consisting of a perfume, a toilet water, an eau de cologne, a pre-shave gel, a pre-shave lotion, an after-shave gel and an after-shave lotion, said composition comprising a natural essence containing a phototoxic dose of furocoumarin and an amount of about 0.01 to 2% by weight of at least one benzylidenecamphor derivative filtering out UV-A radiation and reducing the phototoxicity of said furocoumarin selected from the group consisting of:

the 3-p-oxybenzylidenebornan-2-ones of the formula:

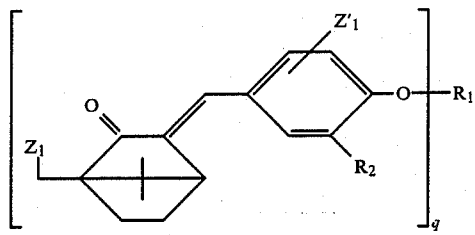

in which:

$Z_1$ and $Z'_1$ respectively denote a hydrogen atom, a radical $SO_3H$ or a salt of this sulphonic acid with an inorganic or organic base, at least one of the two radicals $Z_1$ or $Z'_1$ representing a hydrogen atom; $R_1$ denotes a hydrogen atom, an optionally branched alkyl radical containing 2 to 18 carbon atoms, an alkenyl radical containing 3 to 18 carbon atoms or a radical $-(CH_2CH_2O)_nH$, $-(CH_2CHO)_n-H$, $-CH_2-CHOH-CH_3$,
                                $|$
                                $CH_2OH$

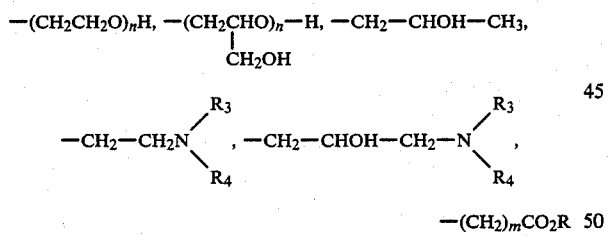

$-(CH_2)_mCO_2R$ in which R denotes H, an alkyl radical containing 1 to 8 carbon atoms, $-(CH_2)_3-SO_3H$ or a salt of this acid with an organic or inorganic base, or alternatively a divalent radical $-(CH_2)_m$ or $-CH_2-CHOH-CH_2$, m having the values 1 to 10 and n having the values 1 to 6, and $R_3$ and $R_4$ each representing a hydrogen atom or an optionally branched or hydroxylated alkyl radical, or together forming an aminoaliphatic heterocycle with the nitrogen atom; $R_2$ denotes a hydrogen atom, an alkoxy radical containing 1 to 4 carbon atoms or a divalent radical $-O-$ joined to the radical $R_1$ in the case where the latter is also divalent; and q denotes 1 or 2, it being understood that if q has the value 2, $R_1$ is a divalent radical, and that if $R_1$ denotes hydrogen, $R_2$ also denotes hydrogen; moreover, if $R_2$ denotes alkoxy, $R_1$ can also denote methyl;

the benzylidenecamphor derivatives of the formula:

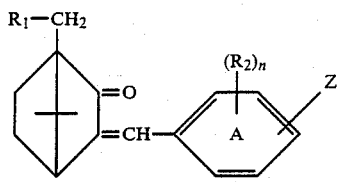

in which:

$R_1$ denotes a hydrogen atom or a radical $-SO_3^{\ominus}M^{\oplus}$, in which M denotes a hydrogen atom, an alkali metal or a group $^{\oplus}N(R_3)_4$, $R_3$ denoting a hydrogen atom or a $C_1$ to $C_4$ alkyl or hydroxyalkyl radical;

n=0, that is to say $R_2$ denotes a hydrogen atom; and

Z represents a group

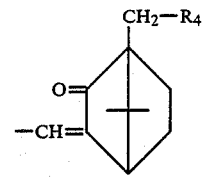

in which $R_4$ has the same meanings as $R_1$ and can be equal to $R_1$ or different from $R_1$, or alternatively a group

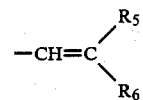

in which $R_5$ denotes a hydrogen atom, a $C_1$ to $C_4$ alkyl radical, an aryl radical optionally substituted by halogen atoms or by $C_1$ to $C_4$ alkyl or alkoxy groups, or a group $-CN$, $-COOR_7$ or

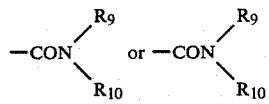

and $R_6$ denotes a group $-COOR_8$, $R_7$ and $R_8$, which are identical or different, being alkyl, alkenyl, cycloalkyl or aralkyl radicals containing at most 20 carbon atoms, which are optionally substituted by hydroxyl, alkoxy, or amine, and $R_9$ and $R_{10}$, which are identical or different, denoting a hydrogen atom or alkyl, alkenyl, cycloalkyl or aralkyl radicals containing at most 20 carbon atoms, which are optionally substituted by hydroxyl, alkoxy, or amine, or alternatively if $R_5$ denotes a hydrogen atom or an alkyl or optionally substituted aryl radical, $R_6$ can also represent a radical $-COO^-M^+$, M being defined as above, the two methylidenecamphor radicals, on the one hand, and Z, on the other hand, being attached to the aromatic nucleus A in the para position relative to one another;

the sulphonamides derived from 3-benzylidenecamphor of the formula:

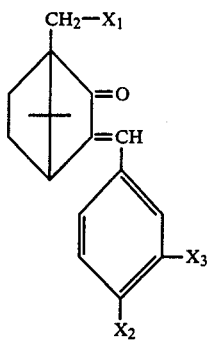

in which:
X₁ denotes the radical Y;
X₂ denotes a radical Z; and
X₃ denotes a hydrogen atom,
Y denoting the group

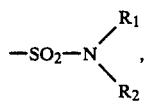

in which $R_1$ denotes a hydrogen atom or a $C_1$–$C_4$ alkyl or hydroxyalkyl radical and $R_2$ denotes a hydrogen atom, a linear or branched alkyl or alkenyl radical or a cycloalkyl, aryl or aralkyl radical, it being possible for these various $C_1$–$C_{20}$ radicals t be substituted by one or more hydroxyl, alkoxy or dialkylamino groups, it being impossible for $R_1$ and $R_2$ simultaneously to denote a hydrogen atom, and Z denoting one of the following groups:

$Z_1 =$

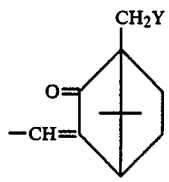

in which Y has the above-mentioned meaning, or
$Z_2 =$

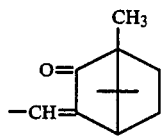

2. Composition according to claim 1, which contains, as the benzylidenecamphor derivative filtering out UV-A radiation, at least one compound selected from the group consisting of: 4'-butoxy-3'-methoxy-3-benzylidenebornanone, 3,3'-terephthalylidenedicampho-10,10'-disulphonic acid, 3,3'-terephthalylidenedicampho-10-sulphonic acid, 4-(ethyl 2'-carboxyethylacrylate)benzylidenecamphor and also their salts.

3. Composition according to claim 1 which contains at least one compound filtering out UV-B radiation which is compatible with the UV-A filters mentioned in claim 1 and is selected from the group consisting of:
benzylidenecamphor;
p-methylbenzylidenecamphor;
benzylidenecamphor derivatives containing a quaternary ammonium radical on the benzene nucleus in the para position relative to the bornylidene radical, of the formula:

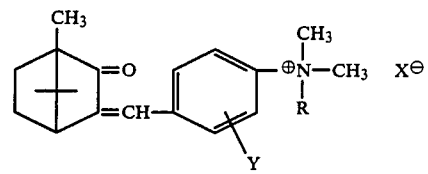

in which:
R represents a hydrogen atom or an alkyl group containing 1 to 12 carbon atoms,
Y represents a halogen, a methyl group or a hydrogen atom, and
X⊖ represents a halide, an arylsulphonate, an alkylsulphonate, a camphosulphonate or an alkylsulphate;
benzylidenecamphor derivatives sulphonated on the methyl radical in the 10-position of the camphor or in the 3'-position or 4'-position on the benzene nucleus, having the formulae:

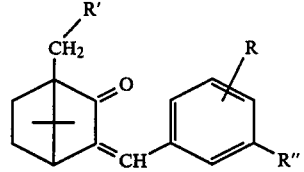

in which R denotes a hydrogen atom, a halogen atom, or an alkyl radical containing 1 to 4 carbon atoms, and R' and R'' each denote a hydrogen atom or a radical —SO₃M, in which M denotes H, an organic ammonium group or a metal, at least one of the radicals R' and R'' not having the meaning H, and

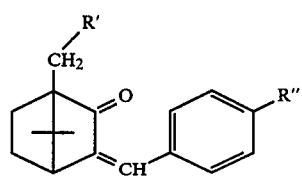

in which R' denotes a hydrogen atom or a radical —SO₃M and R'' denotes SO₃M, in which M denotes H, an organic ammonium group or a metal;
p-methylbenzylidenecamphor derivatives substituted on the p-methyl group, having the formulae:

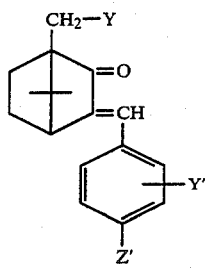

in which Y and Y' denote H or SO₃H and the corresponding salts with organic or inorganic bases, at least one of the radicals Y and Y' having the meaning H; and Z' denotes the group —CH₂R, —CHR'R', —CHO or —COOR", in which R=—OR₄, —OCOR₅, —SR₆, —CN or —COOR", R₄=H, alkyl, polyoxyethylene or unsubstituted aryl, R₅=alkyl, alkenyl, aryl and R₆=H, alkyl, carboxyalkyl, amino-alkyl, hydroxyalkyl, aryl or alanin-3-yl, R'=—OR'₄ or —SR'₆, in which R'₄ and R'₆ can respectively have the same meanings as R₄ and R₆, except for the meaning hydrogen, and R"=hydrogen or alkyl, and

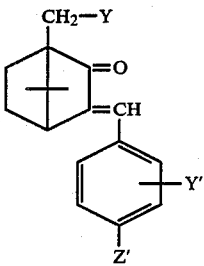

in which Y denotes H or SO₃H and the corresponding salts with organic or inorganic bases; Y' denotes H; and
Z' denotes the group —CH₂I, —CH₂R, —CHR'R', —CHO or —COOR", in which R=OR₄, —OCOR₅, —SR₆, —CN or —COOR", R₄=H, alkyl, polyoxyethylene, or unsubstituted aryl, menthyl or dialkylaminoalkyl, R₅=alkyl, alkenyl, aryl, and R₆=H, alkyl, carboxyalkyl, aminoalkyl, hydroxyalkyl, aryl or alanin-3-yl, R'=—OR'₄ or —SR'₆, in which R'₄ and R'₆ can respectively have the same meanings as R₄ and R₆, except for the meanings hydrogen, polyoxyethylene, hydroxyalkyl, alanin-3-yl and aryl, and R"=hydrogen or alkyl;
the benzylidenecamphor derivatives of the formula:

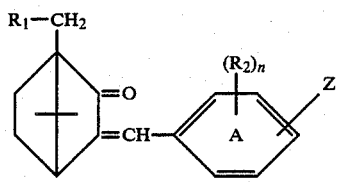

in which:
R₁ denotes a hydrogen atom or a radical —SO₃⊖M⊕, in which M denotes a hydrogen atom, an alkali metal or a group N⊕(R₃)₄, R₃ denoting a hydrogen atom or a C₁ to C₄ alkyl or hydroxyalkyl radical;

R₂ denotes a linear or branched C₁ to C₄ alkyl radical or a C₁ to C₄ alkoxy radical, n being an integer ranging from 0 to 4; if n≧2, the radicals R₂ can be identical or different; and Z represents a group

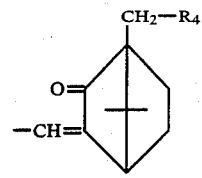

in which R₄ has the same meanings as R₁ and can be equal to R₁ or different from R₁, or alternatively a group

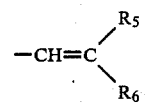

in which R₅ denotes a hydrogen atom, a C₁ to C₄ alkyl radical, an aryl radical optionally substituted by halogen atoms or by C₁ to C₄ alkyl or alkoxy groups, or a group —CN, —COOR₇ or

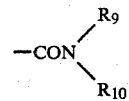

and R₆ denotes a group —COOR₈ or

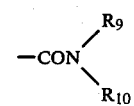

R₇ and R₈, which are identical or different, being alkyl, alkenyl, cycloalkyl or aralkyl radicals containing at most 20 carbon atoms, which are optionally substituted by hydroxyl, alkoxy, or amine, and R₉ and R₁₀, which are identical or different, denoting a hydrogen atom or alkyl, alkenyl, cycloalkyl or aralkyl radicals containing at most 20 carbon atoms, which are optionally substituted by hydroxyl, alkoxy, or amine, or alternatively if R₅ denotes a hydrogen atom or an alkyl or optionally substituted aryl radical, R₆ can also represent a radical —COO⊖M⊕, M being defined as above,
the two methylidenecamphor radicals, on the one hand, and Z, on the other hand, being attached to the aromatic nucleus A in the meta position relative to one another; they can be attached in the para position if n≠0;
the sulphonamides derived from 3-benzylidenecamphor of the formula:

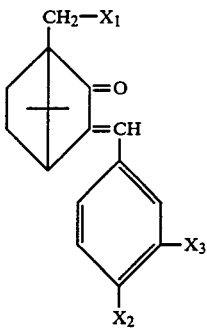

in which $X_1$ denotes a hydrogen atom or the radical Y; $X_2$ denotes a hydrogen or halogen atom, a $C_1$-$C_4$ alkyl or alkoxy radical or a radical Y or Z; and $X_3$ denotes a hydrogen or halogen atom, a $C_1$-$C_4$ alkyl or alkoxy radical or a radical Y or Z, or alternatively $X_2$ and $X_3$ together form an alkylenedioxy group in which the alkylene group contains 1 or 2 carbon atoms,
Y denoting the group

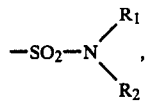

in which $R_1$ denotes a hydrogen atom or a $C_1$-$C_4$ alkyl or hydroxyalkyl radical and $R_2$ denotes a hydrogen atom, a linear or branched alkyl or alkenyl radical or a cycloalkyl, aryl or aralkyl radical, it being possible for these various $C_1$-$C_{20}$ radicals to be substituted by one or more hydroxyl, alkoxy or dialkylamino groups, it being impossible for $R_1$ and $R_2$ simultaneously to denote a hydrogen atom, and Z denoting one of the following groups:
$Z_1=$

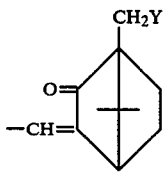

in which Y has the abovementioned meaning, or
$Z_2=$

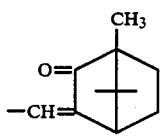

or
$Z_3=$

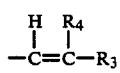

in which $R_3$ denotes a hydrogen atom or a group —CN or —COR$_5$ and $R_4$ denotes a group —COR$_6$, $R_5$ and $R_6$, which are identical or different, being $C_1$-$C_{20}$ alkoxy or alkylamino groups, with the proviso that one of the symbols $X_1$, $X_2$ and $X_3$ is different from the other two and that
(a) when $X_1$ denotes a hydrogen atom, $X_2$ and $X_3$ are different from one another and cannot take the meanings $Z_2$ and $Z_3$, one of the two necessarily having the meaning Y or $Z_1$, and
(b) when $X_1$ has the meaning Y, $X_2$ and $X_3$ are different from Y and cannot simultaneously take the meaning $Z_1$, $Z_2$ or $Z_3$, and moreover, if $X_2 Z_1$ or $Z_2$, $X_3$ does not denote a hydrogen atom.

4. Composition according to claim 3, which contains, as compounds filtering out UV-B radiation, at least one compound selected from the group consisting of: benzylidenecamphor, 4-[(2-oxo-3-bornylidene)-methyl]-phenyltrimethylammonium methyl-sulphate, p-methyl-benzylidenecamphor, N-(2-ethylhexyl)-3-benzylidenecampho-10-sulphonamide, 3-benzylidene-2-oxobornane-10-sulphonic acid, 3-(2-oxo-3-bornylidenemethyl)-benzenesulphonic acid, 2-methyl-5-(2-oxo-3-bornylidenemethyl)benzenesulphonic acid and also their salts.

5. Composition according to claim 1, wherein the natural essence is chosen from bergamot oil and lemon oil.

6. Composition according to claim 1, which contains 0.1 to 1% by weight of benzylidenecamphor derivatives, relative to the total weight of the composition.

7. Composition according to claim 1 which is in the form of an alcoholic or aqueous-alcoholic gel comprising, in addition to the natural essence, one or more lower alcohols selected from the group consisting of ethanol, propylene glycol and glycerol, and a thickener.

8. Composition according to claim 1, which constitutes an aqueous-alcoholic solution containing, in addition to the natural essence, a lower alkanol containing 1 to 4 carbon atoms selected from the group consisting of ethanol, isopropanol and n-propanol, and comprising adjuvants selected from the group consisting of softeners, cicatrising agents and preservatives.

9. A process for reducing the phototoxicity of an alcoholic or aqueous-alcoholic composition in a form selected from the group consisting of a perfume, a toilet water, an eau de cologne, a pre-shave gel, a pre-shave lotion, an after-shave gel and an after-shave lotion, said composition comprising a natural essence containing a phototoxic dose of furocoumarin, comprising incorporating into said composition an amount of about 0.01 to 2% by weight of at least one benzylidenecamphor derivative filtering out UV-A radiation and reducing the phototoxicity of said furocoumarin selected from the group consisting of:
the 3-p-oxybenzylidenebornan-2-ones of the formula:

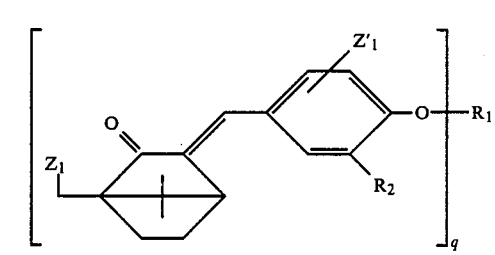

in which:

$Z_1$ and $Z'_1$ respectively denote a hydrogen atom, a radical $SO_3H$ or a salt of this sulphonic acid with an inorganic or organic base, at least one of the two radicals $Z_1$ or $Z'_1$ representing a hydrogen atom; $R_1$ denotes a hydrogen atom, an optionally branched alkyl radical containing 2 to 18 carbon atoms, an alkenyl radical containing 3 to 18 carbon atoms or a radical

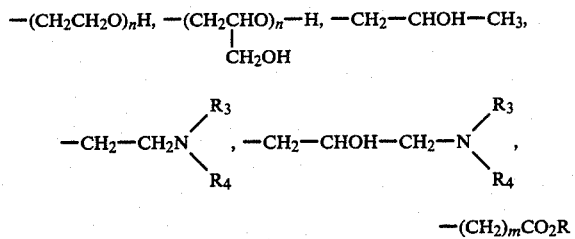

$$-(CH_2)_m CO_2 R$$

in which R denotes H, an alkyl radical containing 1 to 8 carbon atoms, $-(CH_2)_3-SO_3H$ or a salt of this acid with an organic or inorganic base, or alternatively a divalent radical $-(CH_2)_m$ or $-CH_2-CHOH-CH_2-$, m having the values 1 to 10 and n having the values 1 to 6, and $R_3$ and $R_4$ each representing a hydrogen atom or an optionally branched or hydroxylated alkyl radical, or together forming an aminoaliphatic heterocycle with the nitrogen atom; $R_2$ denotes a hydrogen atom, an alkoxy radical containing 1 to 4 carbon atoms or a divalent radical $-O-$ joined to the radical $R_1$ in the case where the latter is also divalent; and q denotes 1 to 2, it being understood that if q has the value 2, $R_1$ is a divalent radical, and that if $R_1$ denotes hydrogen, $R_2$ also denotes hydrogen; moreover, if $R_2$ denotes a alkoxy, $R_1$ can also denote methyl;

the benzylidenecamphor derivatives of the formula:

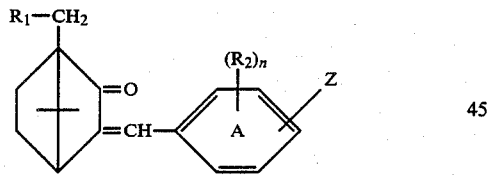

in which: $R_1$ denotes a hydrogen atom or a radical $-SO_3^{\ominus}M^{\oplus}$, in which M denotes a hydrogen atom, an alkali metal or a group $^{\oplus}N(R_3)_4$, $R_3$ denoting a hydrogen atom or a $C_1$ to $C_4$ alkyl or hydroxyalkyl radical;

n=0, that is to say $R_2$ denotes a hydrogen atom; and Z represents a group

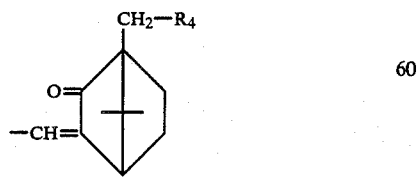

in which $R_4$ has the same meanings as $R_1$ and can be equal to $R_1$ or different from $R_1$, or alternatively a group

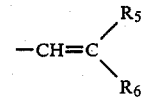

in which $R_5$ denotes a hydrogen atom, a $C_1$ to $C_4$ alkyl radical, an aryl radical optionally substituted by halogen atoms or by $C_1$ to $C_4$ alkyl or alkoxy groups, or a group

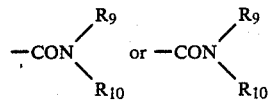

and $R_6$ denotes a group $-COOR_8$, $R_7$ and $R_8$, which are identical or different, being alkyl, alkenyl, cyloalkyl or aralkyl radicals containing at most 20 carbon atoms, which are optionally substituted by hydroxyl, alkoxy, or amine, and $R_9$ and $R_{10}$, which are identical or different, denoting a hydrogen atom or alkyl, alkenyl, cycloalkyl or aralkyl radicals containing at most 20 carbon atoms, which are optionally substituted by hydroxyl, alkoxy, or amine or alternatively if $R_5$ denotes a hydrogen atom or an alkyl or optionally substituted aryl radical, $R_6$ can also represent a radical $-COO^-M^+$, M being defined as above, the two methylidenecamphor radicals, on the one hand, and Z, on the other hand, being attached to the aromatic nucleus A in the para position relative to one another;

the sulphonamides derived from 3-benzylidenecamphor of the formula:

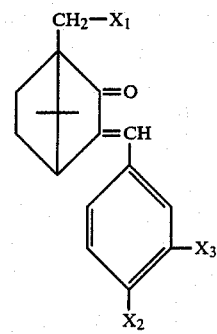

in which:
$X_1$ denotes the radical Y;
$X_2$ denotes the radical Z; and
$X_3$ denotes a hydrogen atom,
Y denoting the group

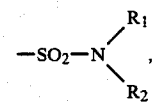

in which $R_1$ denotes a hydrogen atom or a $C_1-C_4$ alkyl or hydroxyalkyl radical and $R_2$ denotes a hydrogen atom, a linear or branched alkyl or alkenyl radical or a cycloalkyl, aryl or aralkyl radical, it being possible for these various $C_1-C_{20}$ radicals to be substituted by one or more hydroxyl, alkoxy or dialkylamino groups, it being impossible for $R_1$ and $R_2$ simultaneously to denote a hydrogen atom, and Z denoting one of the following groups:

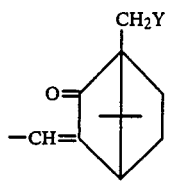

in which Y has the above-mentioned meaning, or $Z_2=$

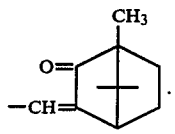

10. A composition according to claim 8 which further comprises glycols selected from the group consisting of ethylene glycol and propylene glycol.

11. The process of claim 9 wherein the benzylidenecamphor derivative filtering out UV-A radiation is selected from the group consisting of 4'-butoxy-3'-methoxy-3-benzylidene-bornanone, 3,3'-terephthalylidenedicampho-10,10'-disulphonic acid, 3,3'-terephthalylidenedicampho-10-sulphonic acid, 4-(ethyl 2'-carboxyethylacrylate)-benzylidenecamphor and also their salts.

12. The process of claim 9 wherein the process further comprises incorporating at least one compound filtering out UV-B radiation which is compatible with the UV-A filters mentioned in claim 9 and is selected from the group consisting of:
benzylidenecamphor;
p-methylbenzylidenecamphor;
benzylidenecamphor derivatives containing a quaternary ammonium radical on the benzene nucleus in the para position relative to the bornylidene radical, of the formula:

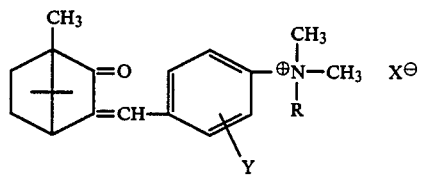

in which:
R represents a hydrogen atom or an alkyl group containing 1 to 12 carbon atoms,
Y represents a halogen, a methyl group or a hydrogen atom, and
$X^\ominus$ represents a halide, an arylsulphonate, an alkylsulphonate, a camphosulphonate or an alkylsulphate;
benzylidenecamphor derivatives sulphonated on the methyl radical in the 10-position of the camphor or in the 3'-position or 4'-position on the benzene nucleus, having the formulae:

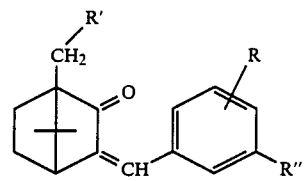

in which R denotes a hydrogen atom, a halogen atom, or an alkyl radical containing 1 to 4 carbon atoms, and R' and R" each denote a hydrogen atom or a radical —$SO_3M$, in which M denotes H, an organic ammonium group or a metal, at least one of the radicals R' and R" not having the meaning H, and

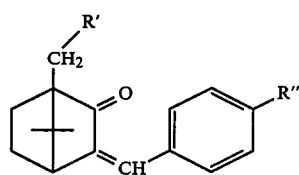

in which R' denotes a hydrogen atom or a radical —$SO_3M$ and R" denotes $SO_3M$, in which M denotes H, an organic ammonium group or a metal;
p-methylbenzylidenecamphor derivatives substituted on the p-methyl group, having the formulae:

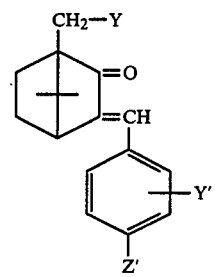

in which Y and Y' denote H or $SO_3H$ and the corresponding salts with organic or inorganic bases, at least one of the radicals Y and Y' having the meaning H; and Z' denotes the group —$CH_2R$, —CHR'R', —CHO or —COOR", in which R=—$OR_4$, —$OCOR_5$, —$SR_6$, —CN or —COOR", $R_4$=H, alkyl, polyoxyethylene or unsubstituted aryl, $R_5$=alkyl, alkenyl, aryl and $R_6$=H, alkyl, carboxyalkyl, aminoalkyl, hydroxyalkyl, aryl or alanin-3-yl, R'=—$OR'_4$ or —$SR'_6$, in which $R'_4$ and $R'_6$ can respectively have the same meanings as $R_4$ and $R_6$, except for the meaning hydrogen, and R"=hydrogen or alkyl, and

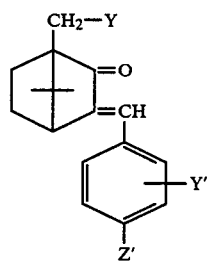

in which Y denotes H or $SO_3H$ and the corresponding salts with organic or inorganic bases;

Y' denotes H; and

Z' denotes the group $-CH_2I-CH_2R$, $-CHR'R'$, $-CHO$ or $-COOR''$, in which $R=OR_4$, $-OCOR_5$, $-SR_6$, $-CN$ or $-COOR''$, $R_4=H$, alkyl, polyoxyethylene, or unsubstituted aryl, menthyl or dialkylaminoalkyl, $R_5$=alkyl, alkenyl, aryl, and $R_6$=H, alkyl, carboxyalkyl, aminoalkyl, hydroxyalkyl, aryl or alanin-3-yl, $R'=-OR'_4$ or $-SR'_6$, in which $R'_4$ and $R'_6$ can respectively have the same meanings as $R_4$ and $R_6$, except for the meanings hydrogen, polyoxyethylene, hydroxyalkyl, alanin-3-yl and aryl, and $R''$=hydrogen or alkyl;

the benzylidenecamphor derivatives of the formula:

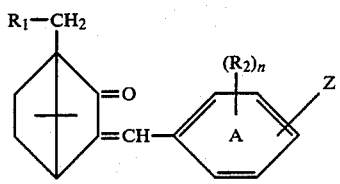

in which:

$R_1$ denotes a hydrogen atom or a radical $-SO_3^{\ominus}M^{\oplus}$, in which M denotes a hydrogen atom, an alkali metal or a group $N^{\oplus}(R_3)_4$, $R_3$ denoting a hydrogen atom or a $C_1$ to $C_4$ alkyl or hydroxyalkyl radical;

$R_2$ denotes a linear or branched $C_1$ to $C_4$ alkyl radical or a $C_1$ to $C_4$ alkoxy radical, n being an integer ranging from 0 to 4; if $n \geq 2$, the radicals $R_2$ can be identical or different; and Z represents a group

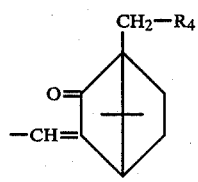

in which $R_4$ hs the same meanings as $R_1$ and can be equal to $R_1$ or different from $R_1$, or alternatively a group

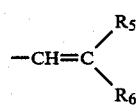

in which $R_5$ denotes a hydrogen atom, a $C_1$ to $C_4$ alkyl radical, an aryl radical optionally substituted by halogen atoms or by $C_1$ to $C_4$ alkyl or alkoxy groups, or a group $-CN$, $-COOR_7$ or

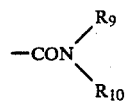

and $R_6$ denotes a group $-COOR_8$ or

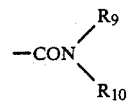

$R_7$ and $R_8$, which are identical or different, being alkyl, alkenyl, cycloalkyl or aralkyl radicals containing at most 20 carbon atoms, which are optionally substituted by hydroxyl, alkoxy, or amine, and $R_9$ and $R_{10}$, which are identical or different, denoting a hydrogen atom or alkyl, alkenyl, cycloalkyl or aralkyl radicals containing at most 20 carbon atoms, which are optionally substituted by hydroxyl, alkoxy, or amine, or alternatively if $R_5$ denotes a hydrogen atom or an alkyl or optionally substituted aryl radical, $R_6$ can also represent a radical $-COO^{\ominus}M^{\oplus}$, M being defined as above, the two methylidenecamphor radicals, on the one hand, and Z, on the other hand, being attached to the aromatic nucleus A in the meta position relative to one another; they can be attached in the para position if $n \neq 0$;

the sulphonamides derived from 3-benzylidenecamphor of the formula:

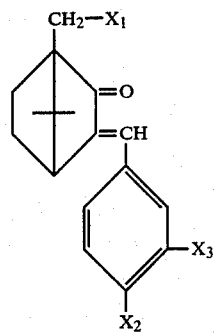

in which $X_1$ denotes a hydrogen atom or the radical Y; $X_2$ denotes a hydrogen or halogen atom, a $C_1$ to $C_4$ alkyl or alkoxy radical or a radical Y or Z; and $X_3$ denotes a hydrogen or halogen atom, a $C_1$ to $C_4$ alkyl or alkoxy radical or a radical Y or Z, or alternatively $X_2$ and $X_3$ together form an alkylenedioxy group in which the alkylene group contains 1 or 2 carbon atoms, Y denoting the group

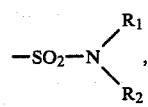

in which $R_1$ denotes a hydrogen atom or a $C_1$ to $C_4$ alkyl or hydroxyalkyl radical and $R_2$ denotes a hydrogen atom, a linear or branched alkyl or alkenyl radical or a cycloalkyl, aryl or aralkyl radical, it being possible for these various $C_1$ to $C_{20}$ radicals to be substituted by one or more hydroxyl, alkoxy or dialkylamino groups, it being impossible for $R_1$ and $R_2$ simultaneously to denote a hydrogen atom, and Z denoting one of the following groups:

$Z_1=$

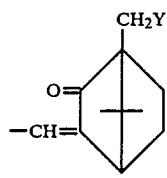

in which Y has the above-mentioned meaning, or
$Z_2 =$

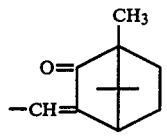

or
$Z_3 =$

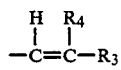

in which $R_3$ denotes a hydrogen atom or a group $-CN$ or $-COR_5$ and $R_4$ denotes a group $-COR_6$, $R_5$ and $R_6$, which are identical or different, being $C_1$ to $C_{20}$ alkoxy or alkylamino groups, with the proviso that one of the symbols $X_1$, $X_2$ and $X_3$ is different from the other two and that (a) when $X_1$ denotes a hydrogen atom, $X_2$ and $X_3$ are different from one another and cannot take the meanings $Z_2$ and $Z_3$, one of the two necessarily having the meaning Y or $Z_1$, and (b) when $X_1$ has the meaning Y, $X_2$ and $X_3$ are different from Y and cannot simultaneously take the meaning $Z_1$, $Z_2$ or $Z_3$, and moreover, if $X_2$, $Z_1$ or $Z_2$, $X_3$ does not denote a hydrogen atom.

13. The process of claim 11 wherein the compound filtering out UV-B radiation is selected from the group consisting of benzylidenecamphor, 4-[(2-oxo-3-bornylidene)methyl]-phenyltrimethylammonium methylsulphate, p-methylbenzylidenecamphor, N-(2-ethylhexyl)-3-benzylidenecampho-10-sulphonamide, 3-benzylidene-2-oxobornane-10-sulphonic acid, 3-(2-oxo-3-bornylidenemethyl)-benzenesulphonic acid, 2-methyl-5-(2-oxo-3-bornylidenemethyl)-benzenesulphonic acid and also their salts.

14. The process of claim 9 wherein the natural essence is chosen from bergamot oil and lemon oil.

15. The process of claim 9 which comprises incorporating 0.1 to 1% by weight of benzylidenecamphor derivatives.

16. The process of claim 9 wherein the composition is in the form of an alcoholic or aqueous-alcoholic gel comprising, in addition to the natural essence, one or more lower alcohols selected from the group consisting of ethanol, propylene glycol and glycerol, and a thickener.

17. The process of claim 9 wherein the composition constitutes an aqueous-alcoholic solution containing, in addition to the natural essence, a lower alkanol containing 1 to 4 carbon atoms selected from the group consisting of ethanol, isopropanol and n-propanol, and comprising adjuvants selected from the group consisting of softeners, cicatrising agents and preservatives.

18. The process of claim 16 wherein the composition further comprises glycols selected from the group consisting of ethylene glycol and propylene glycol.

* * * * *